US012773095B2

(12) United States Patent
Asaoka et al.

(10) Patent No.: US 12,773,095 B2
(45) Date of Patent: Oct. 27, 2026

(54) ENDOSCOPE

(71) Applicant: FUJIFILM Corporation, Tokyo (JP)

(72) Inventors: Takuro Asaoka, Kanagawa (JP); Takeshi Yukiiri, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 598 days.

(21) Appl. No.: 18/358,971

(22) Filed: Jul. 26, 2023

(65) Prior Publication Data

US 2024/0081620 A1 Mar. 14, 2024

(30) Foreign Application Priority Data

Sep. 13, 2022 (JP) ................................ 2022-145498

(51) Int. Cl.
*A61B 1/00* (2006.01)
*A61B 1/012* (2006.01)
(Continued)

(52) U.S. Cl.
CPC .......... *A61B 1/00096* (2013.01); *A61B 1/012* (2013.01); *A61B 1/051* (2013.01); *A61B 1/0669* (2013.01)

(58) Field of Classification Search
CPC ............ A61B 1/00087; A61B 1/00091; A61B 1/00094; A61B 1/00096; A61B 1/00098;
(Continued)

(56) References Cited

U.S. PATENT DOCUMENTS 4,646,721 A * 3/1987 Arakawa .................. A61B 1/05 600/130
4,741,327 A 5/1988 Yabe
(Continued)

FOREIGN PATENT DOCUMENTS

JP S635722 1/1988
JP H0664243 8/1994
(Continued)

OTHER PUBLICATIONS

"Notice of Reasons for Refusal of Japan Counterpart Application", issued on Feb. 10, 2026, with English translation thereof, p. 1-p. 8.

*Primary Examiner* — Michael J Carey
*Assistant Examiner* — Stephen Floyd London
(74) *Attorney, Agent, or Firm* — JCIPRNET

(57) ABSTRACT

Provided is an endoscope with a narrower diameter at a distal end portion of an insertion part to be inserted into a body of a subject.
The endoscope includes: a forceps port; and an imaging unit, in which the forceps port and the imaging unit are disposed side by side at a distal end of the endoscope, the imaging unit includes an imaging lens, an imaging element having a light-receiving surface disposed parallel to an optical axis of the imaging lens, an optical element that bends the optical axis of the imaging lens by 90° to make light that has transmitted through the imaging lens incident on the imaging element, and a holder that holds the imaging lens and the optical element, a forceps pipe connected to the forceps port is disposed on a light-receiving surface side of the imaging element, in a case in which the imaging unit is viewed in a first direction perpendicular to the light-receiving surface of the imaging element, a central axis of the imaging element that passes through a center of an outer shape of the imaging element and is parallel to the optical axis is located closer to a forceps port side than the optical axis is, a part of the forceps pipe connected to the forceps port overlaps the light-receiving surface of the imaging element, and a central axis of the forceps pipe is located outside the imaging element. On a plane that passes through the optical axis and is parallel to the light-receiving surface, a part farthest from the optical axis is opposite to the central axis of the imaging element with respect to the optical axis in a case in which the imaging unit is viewed in the first direction.

18 Claims, 6 Drawing Sheets

(51) Int. Cl.
*A61B 1/05* (2006.01)
*A61B 1/06* (2006.01)

(58) Field of Classification Search
CPC ....... A61B 1/00119; A61B 1/018; A61B 1/05; A61B 1/051; A61B 1/053
See application file for complete search history.

(56) References Cited

U.S. PATENT DOCUMENTS

| | | | | |
|---|---|---|---|---|
| 4,757,805 | A * | 7/1988 | Yabe | A61B 1/051 600/109 |
| 5,427,087 | A * | 6/1995 | Ito | A61B 1/00096 600/128 |
| 7,828,722 | B2 | 11/2010 | Ooyatsu | |
| 10,084,947 | B2 | 9/2018 | Nakamura et al. | |
| 2009/0062616 | A1* | 3/2009 | Nagamizu | G02B 23/2423 600/173 |
| 2011/0245608 | A1* | 10/2011 | Takahashi | A61B 1/051 600/109 |
| 2012/0220825 | A1* | 8/2012 | Kimura | A61B 1/00124 600/109 |
| 2014/0078280 | A1* | 3/2014 | Yoshida | A61B 1/00163 348/76 |
| 2016/0157705 | A1* | 6/2016 | Wataya | A61B 1/00009 600/104 |
| 2017/0255001 | A1* | 9/2017 | Yamashita | A61B 1/051 |
| 2017/0265721 | A1* | 9/2017 | Ichimura | A61B 1/044 |
| 2018/0344132 | A1* | 12/2018 | Kitano | A61B 1/0011 |

FOREIGN PATENT DOCUMENTS

| | | |
|---|---|---|
| JP | 2006204342 | 8/2006 |
| JP | 2013225812 | 10/2013 |

* cited by examiner

ENDOSCOPE

CROSS-REFERENCE TO RELATED APPLICATIONS

The present application claims priority under 35 U.S.C. § 119 to Japanese Patent Application No. 2022-145498, filed on Sep. 13, 2022. The above application is hereby expressly incorporated by reference, in its entirety, into the present application.

BACKGROUND OF THE INVENTION

1. Field of the Invention

The present invention relates to an endoscope that acquires an image of an observation target, and particularly relates to an endoscope in which at least a forceps port and an imaging unit are disposed side by side at a distal end thereof.

2. Description of the Related Art

In recent years, a diagnosis and the like using an endoscope system that comprises a light source device for an endoscope, an endoscope, and a processor device have been widely performed.

An insertion part to be inserted into a body of a subject is provided, and illumination light from the light source device for an endoscope passes through the insertion part and is emitted to an observation target. The endoscope captures an image of the observation target irradiated with illumination light with an imaging element to generate an image signal. The processor device performs image processing on the image signal generated by the endoscope to generate an observation image to be displayed on a monitor. The imaging element is electrically connected to a signal cable via a circuit board formed of a flexible wiring board or the like, and the signal cable is electrically connected to the processor device. As for the endoscope, it required that a distal end portion of the insertion part to be inserted into the body of the subject is thin, because using the thin distal end portion reduces a physical burden on the subject.

For example, JP2006-204342A discloses an endoscope having a configuration in which an endoscope observation unit configured of an illumination portion and an observation portion and a treatment tool outlet port are provided on a distal end surface of a rigid distal end portion of an insertion part connected to a main body operating part, the observation portion including: an objective optical system including an objective lens and a prism for bending an optical axis of the objective lens by 90°; and an imaging assembly joined to the prism and including a solid-state imaging element and a substrate of the solid-state imaging element, and the illumination portion being configured of an illumination lens and a light guide disposed opposite to the illumination lens, in which, in a case in which, on a cross section orthogonal to an axis of the rigid distal end portion, first and second axes orthogonal to each other centering on an axial center of the rigid distal end portion are set, the imaging assembly is disposed to face in a direction parallel to the first axis, and the imaging assembly and an observation center of the objective lens are disposed opposite to each other with the first axis interposed therebetween, the treatment tool outlet port and the observation portion are disposed mainly opposite to each other with the second axis as a boundary, a center of the treatment tool outlet port is disposed at a position between a first plane including a front surface of a portion of the imaging assembly which has the maximum width and a second plane parallel to the first plane and including the observation center of the objective lens, and the illumination portion is disposed on a side where the objective lens is disposed with respect to the second axis and on both sides of the objective lens.

SUMMARY OF THE INVENTION

At present, there is a demand for a further reduction in diameter of the distal end portion of the insertion part to be inserted into the body of the subject, and the endoscope disclosed in JP2006-204342A cannot cope with the further reduction in diameter.

An object of the present invention is to provide an endoscope with a narrower diameter at a distal end portion of an insertion part to be inserted into a body of a subject.

In order to achieve the above-described object, the invention [1] provides an endoscope comprising: a forceps port; and an imaging unit, in which at least the forceps port and the imaging unit are disposed side by side at a distal end of the endoscope, the imaging unit includes an imaging lens, an imaging element having a light-receiving surface disposed parallel to an optical axis of the imaging lens, an optical element that bends the optical axis of the imaging lens by 90° to make light that has transmitted through the imaging lens incident on the imaging element, and a holder that holds the imaging lens and the optical element, a forceps pipe is connected to the forceps port, a forceps tube is connected to the forceps pipe, and the forceps pipe and the forceps tube are disposed on a light-receiving surface side, in a case in which the imaging unit is viewed in a first direction perpendicular to the light-receiving surface of the imaging element, a central axis of the imaging element that passes through a center of an outer shape of the imaging element and is parallel to the optical axis of the imaging lens is located closer to a forceps port side than the optical axis of the imaging lens is, a part of the forceps pipe connected to the forceps port or the forceps tube overlaps the light-receiving surface of the imaging element, and a central axis of each of the forceps pipe and the forceps tube is located outside the imaging element, and on a plane that passes through the optical axis of the imaging lens and is parallel to the light-receiving surface of the imaging element, a part farthest from the optical axis of the imaging lens is opposite to the central axis of the imaging element with respect to the optical axis of the imaging lens in a case in which the imaging unit is viewed in the first direction.

The invention [2] provides the endoscope according to the invention [1], in which $D1<D2$ is satisfied in a case in which $D1$ is a distance between the optical axis of the imaging lens and the part farthest from the optical axis of the imaging lens on the plane that passes through the optical axis of the imaging lens and is parallel to the light-receiving surface of the imaging element in a case in which the imaging unit is viewed in the first direction, and $D2$ is a distance between the optical axis of the imaging lens and a first end portion of the imaging element, which is located on the same side as the central axis of the imaging element, with respect to the optical axis of the imaging lens in a case in which the imaging unit is viewed in the first direction.

The invention [3] provides the endoscope according to the invention [1] or [2], in which $D1-D3>0$ is satisfied in a case in which $D1$ is a distance between the optical axis of the imaging lens and the part farthest from the optical axis of the imaging lens on the plane that passes through the optical axis of the imaging lens and is parallel to the light-receiving surface of the imaging element in a case in which the imaging unit is viewed in the first direction, and D3 is a distance between the optical axis of the imaging lens and a second end portion of the imaging element, which is located on an opposite side to the central axis of the imaging element, with respect to the optical axis of the imaging lens.

The invention [4] provides the endoscope according to any one of the inventions [1] to [3], in which, in a case in which the imaging unit is viewed in the first direction, a central axis of a maximum outer shape in a holding part of the holder that holds the optical element is parallel to the optical axis of the imaging lens, and is opposite to the central axis of the imaging element with respect to the optical axis of the imaging lens.

The invention [5] provides the endoscope according to the invention [4], in which, in a case in which the imaging unit is viewed in the first direction, the optical axis of the imaging lens, the central axis of the imaging element, and the central axis of the holder are parallel to each other, and in a case in which a distance between the central axis of the imaging element and the optical axis of the imaging lens is a first distance, and a distance between the optical axis of the imaging lens and the central axis of the maximum outer shape in the holding part of the holder is a second distance in a direction orthogonal to the optical axis of the imaging lens, the first distance is longer than the second distance.

The invention [6] provides the endoscope according to any one of the inventions [1] to [5], in which a circuit board to which the imaging element is electrically connected is provided, the circuit board includes at least a first plane portion on which the imaging element is mounted and a second plane portion connected to the first plane portion by a first bent portion, and a first axis that passes through a center of an outer shape of the first plane portion and is parallel to the optical axis of the imaging lens and a second axis that passes through a center of an outer shape of the first bent portion and the second plane portion and is parallel to the optical axis of the imaging lens are parallel to each other, and the second axis is opposite to the first axis with the optical axis of the imaging lens interposed therebetween.

The invention [7] provides the endoscope according to the invention [6], in which, in a case in which the imaging unit is viewed in the first direction, a central axis of a maximum outer shape in a holding part of the holder that holds the optical element coincides with the second axis of the circuit board.

The invention [8] provides the endoscope according to any one of the inventions [4] to [7], in which the holding part of the holder that holds the optical element includes a pair of holding members that holds the optical element, and each of the pair of holding members is different in thickness, and, out of the pair of holding members, a holding member on a second axis side of the circuit board with respect to the central axis of the maximum outer shape in the holding part of the holder is thicker.

According to the present invention, it is possible to provide an endoscope with a narrower diameter at a distal end portion of an insertion part to be inserted into a body of a subject.

DESCRIPTION OF THE PREFERRED EMBODIMENTS

Hereinafter, an endoscope according to the embodiment of the present invention will be described in detail based on a preferred embodiment shown in the accompanying drawings.

The figures described below are examples for explaining the present invention, and the present invention is not limited to the figures shown below.

In the following, the term "to" indicating a numerical range includes numerical values described on both sides of the "to". For example, in a case in which c is a numerical value Ca to a numerical value $\varepsilon_\beta$, a range of c is a range including the numerical value Ca and the numerical value $\varepsilon_\beta$ and is represented by $\varepsilon_\alpha \leq \varepsilon \leq \varepsilon_\beta$ in mathematical symbols.

In the following description, the terms "specific angle", "parallel", "perpendicular", "orthogonal", and the like include an error range generally allowed in the relevant technical field.

Endoscope System

An endoscope system irradiates an observation site, such as an inside of a body of a subject which is an observation target, with illumination light (not shown), captures an image of the observation site, generates a display image of the observation site based on an image signal obtained by the imaging, and displays the display image.

Figure 1:
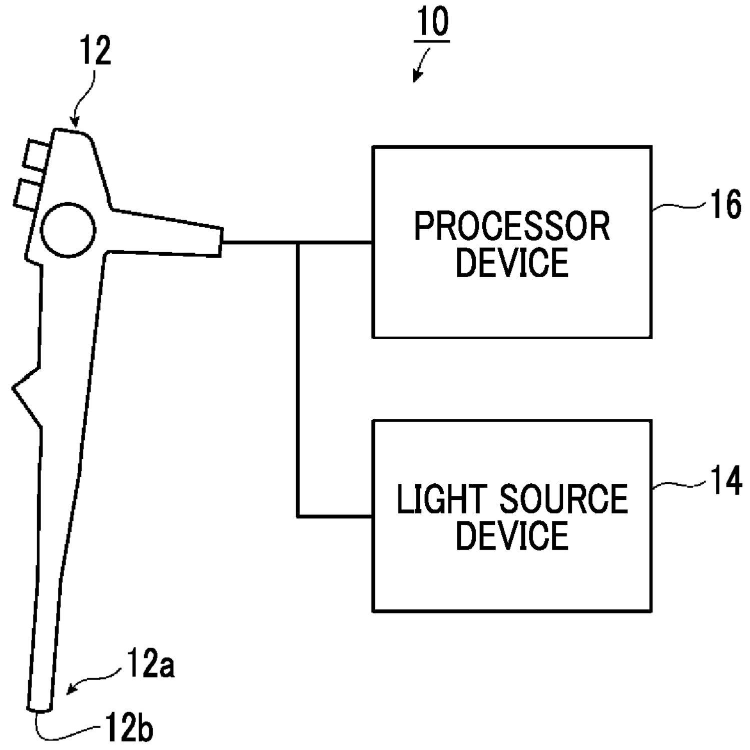
FIG. 1 is a schematic view showing an example of an endoscope system according to an embodiment of the present invention.

FIG. 1 is a schematic view showing an example of an endoscope system according to the embodiment of the present invention, and is a schematic view showing an example of a distal end surface of an example of an endoscope imaging apparatus according to the embodiment of the present invention.

An endoscope system 10 includes an endoscope 12, a light source device 14, and a processor device 16. The endoscope system 10 has the same configuration as a general endoscope except for a portion of an imaging unit **13*b* (see FIG. 2) of the endoscope 12**, which will be described below.

Although not shown in detail, the endoscope 12 includes an insertion part to be inserted into a subject, an operating part that is connected to the insertion part, and a universal cord that extends from the operating part, and the insertion part has a distal end portion, a bendable portion that is connected to the distal end portion, and a soft portion that connects the bendable portion and the operating part. The imaging unit **13*b* (see FIG. 2**) will be described below.

A distal end portion **12*a* of the endoscope 12** is provided with an illumination optical system that emits illumination light with which the observation site is illuminated, or an imaging element and an imaging optical system that capture an image of the observation site. The bendable portion is configured to be bendable in a direction orthogonal to a longitudinal axis of the insertion part, and a bending operation of the bendable portion is performed by the operating part. In addition, the soft portion is configured to be relatively flexible so as to be deformable according to a shape of an insertion path of the insertion part.

The operating part is provided with a button for operating an imaging operation of the imaging unit 13*b* (see FIG. 2) of the distal end portion, or a knob for operating the bending operation of the bendable portion. In addition, the operating part is provided with an introduction port into which a treatment tool, such as an electric scalpel, is introduced, and a treatment tool channel which reaches the distal end portion from the introduction port and through which the treatment tool, such as a forceps, is inserted is provided inside the insertion part.

A connector is provided at a terminal of the universal cord, and the endoscope 12 is connected to the light source device 14 that generates illumination light which is emitted from the illumination optical system of the distal end portion and to the processor device 16 that processes a video signal acquired by the imaging unit 13*b* (see FIG. 2) of the distal end portion 12*a*, via the connector.

The processor device 16 processes the input video signal to generate video data of the observation site, and displays the generated video data on a monitor (not shown) or records the generated video data on a storage medium, such as a hard disk. The processor device 16 may be configured of a processor, such as a personal computer.

The light source device 14 is a light source device for illuminating an observation target site inside a body cavity by generating illumination light, such as white light consisting of three primary color lights, such as red light (R), green light (G), and blue light (B), or specific wavelength light, to supply the generated light to the endoscope 12, by propagating the supplied light through a light guide or the like provided inside the endoscope 12, and by emitting the propagated light from the illumination optical system of the distal end portion of the insertion part of the endoscope 12, in order to acquire the image signal of the observation target by imaging the observation target site inside the body cavity through the imaging unit 13*b* (see FIG. 2) of the endoscope 12.

Figure 2:
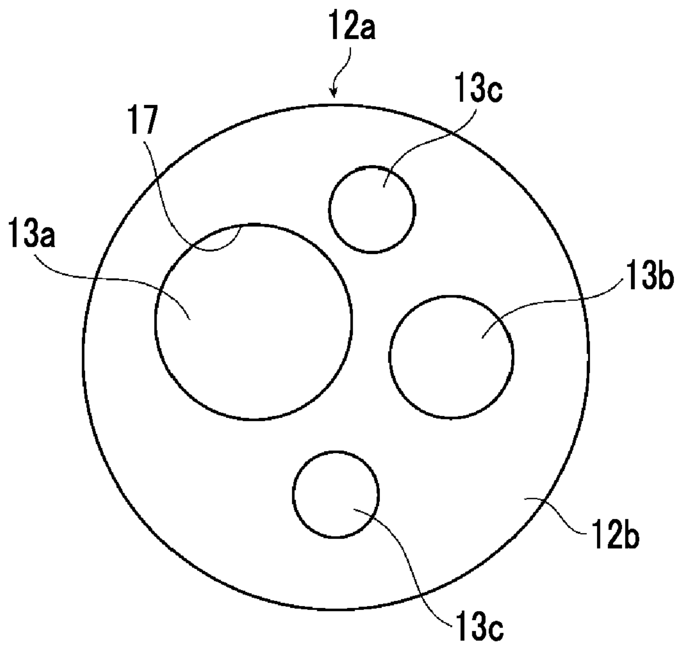
FIG. 2 is a schematic view showing an example of a distal end surface of an example of an endoscope imaging apparatus according to the embodiment of the present invention.

A light guide or an electrical wire group (signal cable) is accommodated inside the insertion part, the operating part, and the universal cord. The illumination light generated by the light source device 14 is guided to the illumination optical system of the distal end portion via the light guide, and the light is emitted from the distal end surface 12*b*. As shown in FIG. 2, at least a forceps port 13*a* and an imaging unit 13*b* are disposed side by side on the distal end surface 12*b* of the distal end portion 12*a*. A light guide 13*c* is also provided on the distal end surface 12*b*. The disposition of the forceps port 13*a*, the imaging unit 13*b*, and the light guide 13*c* on the distal end surface 12*b* is not particularly limited as long as the forceps port 13*a* and the imaging unit 13*b* are disposed side by side. In addition to these, an air/liquid supply nozzle (not shown) may be provided on the distal end surface 12*b*.

A forceps pipe 17 is connected to the forceps port 13*a* integrally or separately. A forceps treatment tool, an injection needle, or the like is housed in the forceps pipe 17. The forceps treatment tool, the injection needle, or the like comes out from the forceps port 13*a*. A forceps tube (not shown) is connected to the forceps pipe 17. The forceps pipe 17 and the forceps tube are made of a metal or a resin.

In addition, the imaging unit 13*b* is configured of, for example, an endoscope imaging apparatus 20 (see FIG. 3) described below. The forceps port 13*a* is disposed on a light-receiving surface 25*a* (see FIG. 2) side of an imaging element 25 (see FIG. 2) of the endoscope imaging apparatus 20.

At least one of a signal or power is transmitted between the endoscope imaging apparatus 20 (see FIG. 3) and the processor device 16 via the electrical wire group.

In addition, the endoscope system 10 may further comprise a water supply tank that stores wash water and the like, a suction pump that sucks a suction substance (also including supplied wash water and the like) in the body cavity, and the like. Further, the endoscope system 10 may comprise a supply pump that supplies wash water in the water supply tank or gas, such as external air, to a pipe line (not shown) in the endoscope, and the like.

Example of Endoscope Imaging Apparatus

Figure 3:
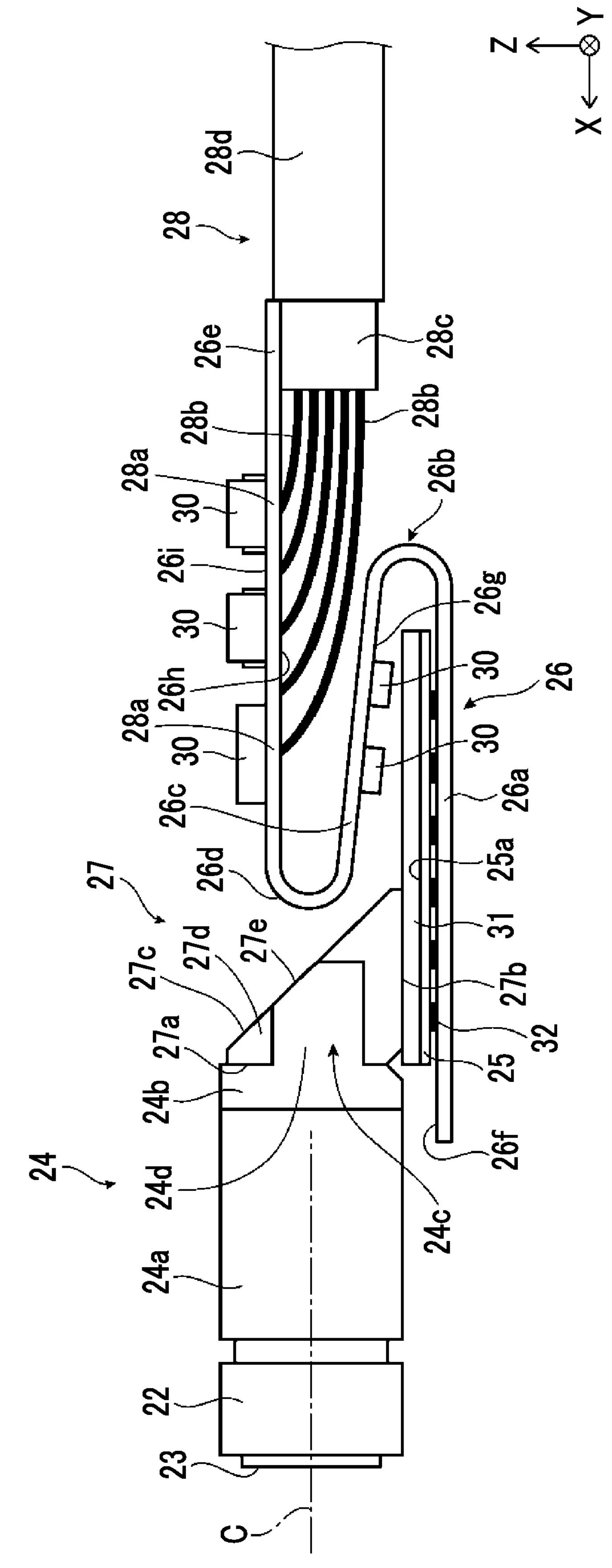
FIG. 3 is a schematic side view showing an example of the endoscope imaging apparatus according to the embodiment of the present invention.
Figure 4:
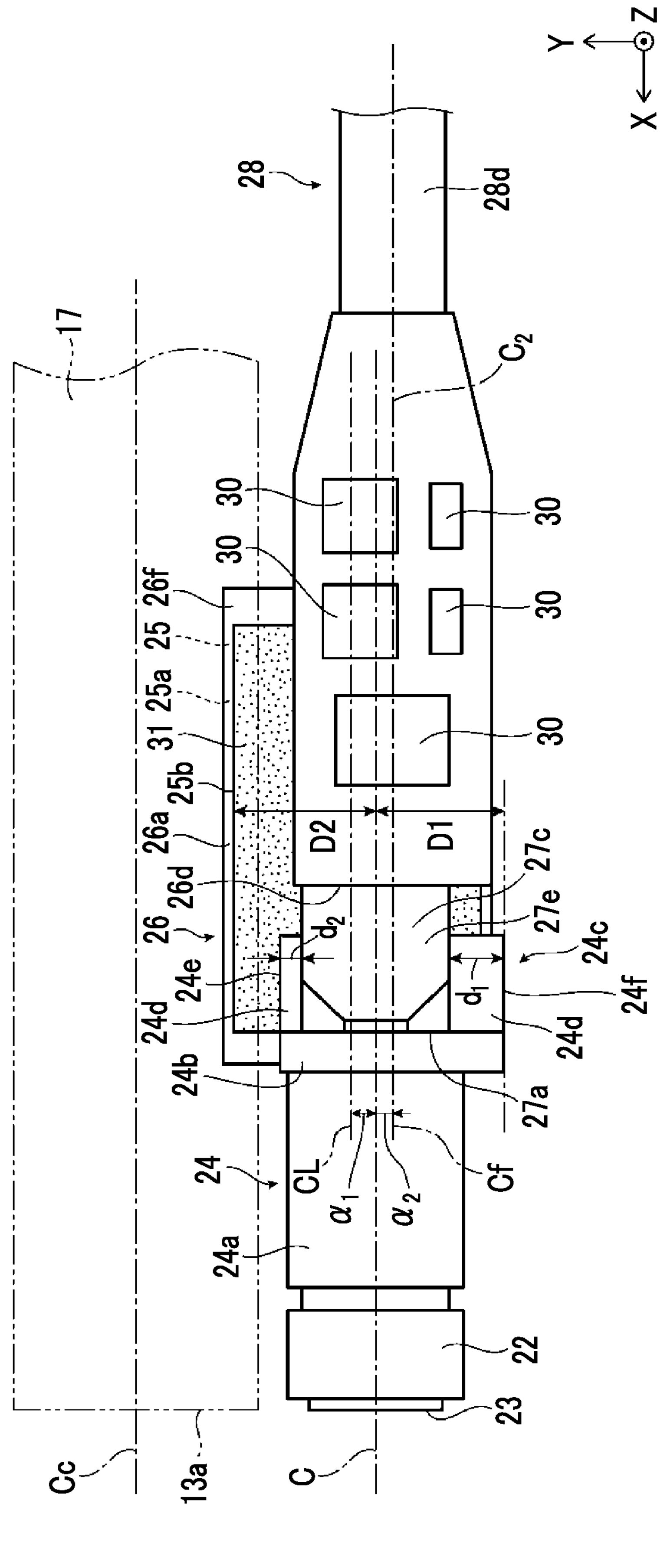
FIG. 4 is a schematic plan view showing an example of the endoscope imaging apparatus according to the embodiment of the present invention.
Figure 5:
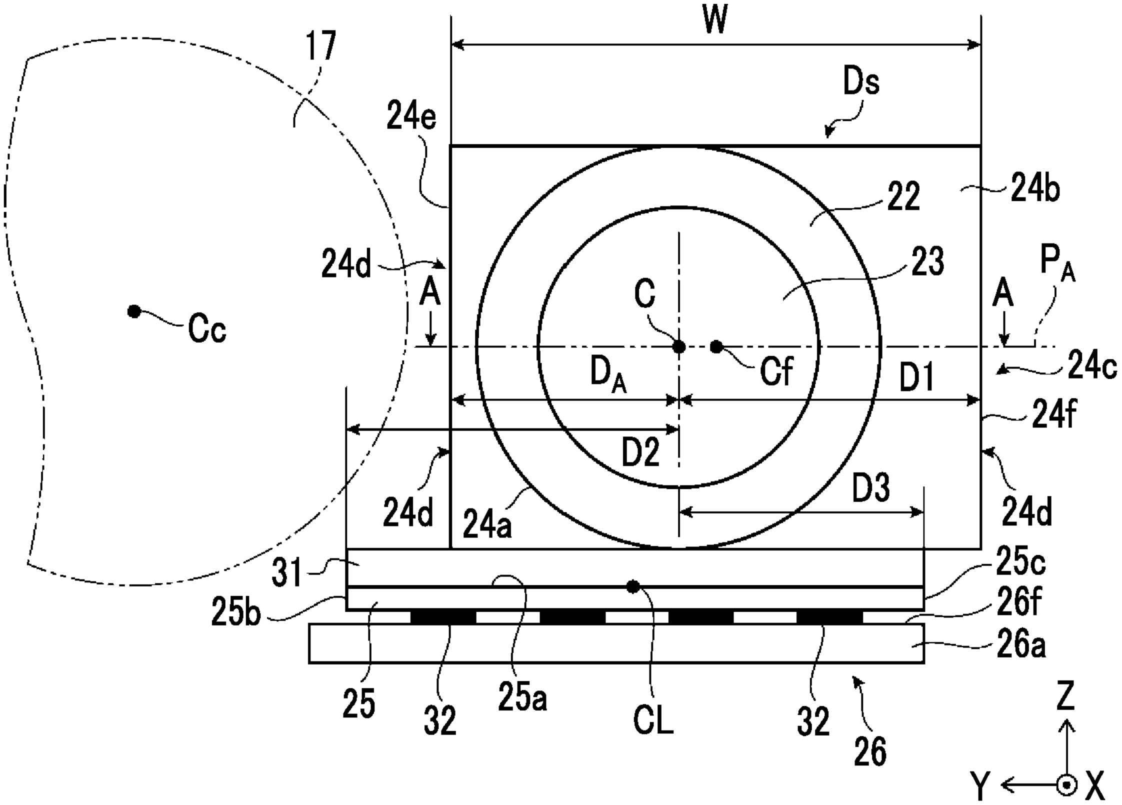
FIG. 5 is a schematic view showing an example of the endoscope imaging apparatus according to the embodiment of the present invention.
Figure 6:
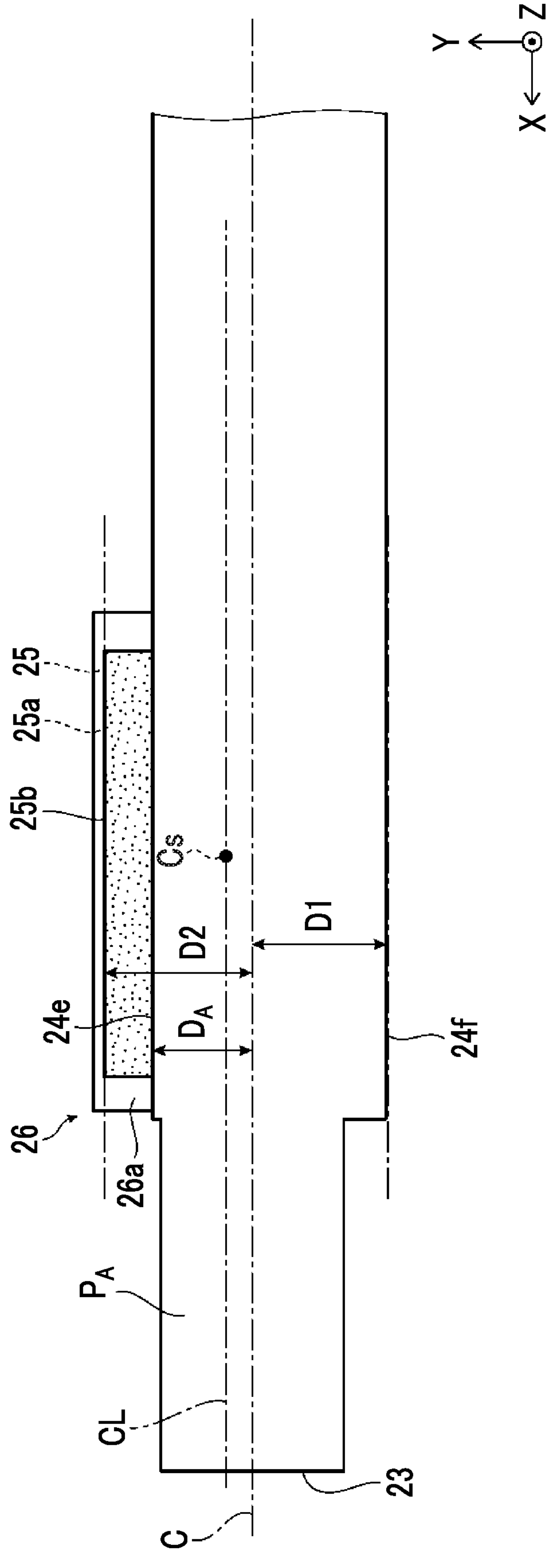
FIG. 6 is a schematic cross-sectional view taken along the line A-A of FIG. 5.

FIG. 3 is a schematic side view showing an example of the endoscope imaging apparatus according to the embodiment of the present invention, FIG. 4 is a schematic plan view showing an example of the endoscope imaging apparatus according to the embodiment of the present invention, and FIG. 5 is a schematic view showing an example of the endoscope imaging apparatus according to the embodiment of the present invention. FIG. 6 is a schematic cross-sectional view taken along the line A-A of FIG. 5. FIG. 4 is a view seen from a first direction, and FIG. 5 is a view seen from an imaging lens 23 side. FIG. 6 is a view seen from the first direction, and a configuration of the endoscope imaging apparatus is not shown.

As described above, the imaging unit 13*b* (see FIG. 2) is configured of the endoscope imaging apparatus 20. Hereinafter, the endoscope imaging apparatus 20 will be described as the imaging unit 13*b*.

The endoscope imaging apparatus 20 acquires an image of the observation target. The endoscope imaging apparatus 20 has, for example, an imaging lens 23, a lens barrel 22 that holds the imaging lens 23, a holder 24, an imaging element 25, a circuit board 26, a prism 27, and a signal cable 28.

Here, a direction parallel to an optical axis C of the imaging lens 23 is denoted by an X direction. Among two directions orthogonal to the optical axis C, one is denoted by a Y direction, and the other is denoted by a Z direction. The Y direction corresponds to a width direction of the endoscope imaging apparatus 20, and the Z direction corresponds to a height direction of the endoscope imaging apparatus 20.

The imaging lens 23 is an optical element that forms an image of light incident into the imaging lens 23 on the light-receiving surface 25*a* of the imaging element 25. The imaging lens 23 is held by the lens barrel 22.

The lens barrel 22 is a tubular member and holds one or more imaging lenses 23 therein. The lens barrel 22 holds the imaging lens 23 such that the optical axis C of the imaging lens 23 is perpendicular to an incident surface 27*a* (see FIG. 3) of the prism 27. The endoscope imaging apparatus 20 has, for example, three imaging lenses 23, and the three imaging lenses 23 are held by the lens barrel 22.

Configurations of the imaging lens 23 and of the lens barrel 22 are not particularly limited. For example, a configuration may be adopted in which one imaging lens 23 is provided, or a configuration may be adopted in which two or four or more imaging lenses 23 are provided. In addition, each imaging lens 23 may be a convex lens or a concave lens.

The imaging element 25 is an imaging element that performs imaging by converting light of which the image is formed by the imaging lens 23 into an electrical signal through photoelectric conversion, and has the light-receiving surface 25*a*. In the imaging element 25, the light of which the image is formed by the imaging lens 23, that is, imaging light of the observation target, is incident on the light-receiving surface 25*a*, and the imaging light is photoelectrically converted, whereby imaging is performed. The imaging element 25 is a conventionally known imaging element, and a charge coupled device (CCD) type image sensor or a complementary metal oxide semiconductor (CMOS) image sensor can be used.

The imaging element 25 is disposed on a side opposite to the lens barrel 22 with respect to the holder 24. As shown in FIG. 3, for example, the imaging element 25 is electrically connected to a front surface 26*f* of a first plane portion 26*a* of the circuit board 26 via a bump 32 having conductivity. In addition, as shown in FIG. 3, the imaging element 25 is mounted on the circuit board 26 with the light-receiving surface 25*a* disposed parallel to the optical axis C of the imaging lens 23. The term "mount" means electrical connection.

The bump 32 is made of a metal or an alloy. More specifically, the bump 32 is made of solder. The bump 32 formed of solder is also referred to as a solder ball. The bump 32 is not limited to solder or the like as long as the imaging element 25 and the circuit board 26 can be electrically connected to each other. In addition, the imaging element 25 and the circuit board 26 may be directly electrically connected to each other.

An underfill layer (not shown) can also be provided between the imaging element 25 and the circuit board 26 in order to firmly connect the imaging element 25 and the circuit board 26 to each other.

Further, a stress is generated in a joint portion between the imaging element 25 and the circuit board 26, for example, in the bump 32 because of a difference in thermal expansion coefficient between the imaging element 25 and the circuit board 26, but the underfill layer relaxes this stress. With the underfill layer, the imaging element 25 and the circuit board 26 are firmly connected to each other, and the reliability of the electrical connection is increased, so that the reliability of the endoscope imaging apparatus 20 is increased.

An underfill agent for forming the underfill layer is not particularly limited, and an underfill agent that is used as a sealing resin between the imaging element 25 and the circuit board 26 can be appropriately used. For example, as the underfill agent, a one-pack heat-curable type epoxy resin is used. In this case, the underfill agent is supplied, and then is heated and held at a predetermined temperature, whereby the underfill layer is formed.

The circuit board 26 is a board on which the imaging element 25 is mounted. In addition, for example, an electronic component 30 is mounted on the circuit board 26, in addition to the imaging element 25. The electronic component 30 is a component for driving the imaging element 25 and is not particularly limited, and examples thereof include a voltage regulator, a resistor, and a capacitor. The voltage regulator is a device that stabilizes a voltage to the imaging element 25, and outputs a constant voltage to the imaging element 25.

As shown in FIG. 3, for example, the circuit board 26 has the first plane portion 26*a*, a second plane portion 26*c* connected by the first plane portion 26*a* and a first bent portion 26*b*, and a third plane portion 26*e* connected by the second plane portion 26*c* and a second bent portion 26*d*. The first plane portion 26*a* and the third plane portion 26*e* are parallel to the optical axis C of the imaging lens 23. The second plane portion 26*c* is angled with respect to the optical axis C of the imaging lens 23, and is inclined with respect to the optical axis C of the imaging lens 23. That is, the second plane portion 26*c* is not parallel to the optical axis C. The second plane portion 26*c* is inclined such that the second bent portion 26*d* is located on an upper side in the Z direction with respect to the first bent portion 26*b*.

In addition, the circuit board 26 has a plurality of connection terminals (not shown) through which a signal or power is input and output to and from the imaging element 25 and the electronic component 30 and which are provided on a back surface 26*h* (see FIG. 3) of the third plane portion 26*e* (see FIG. 3) facing the second plane portion 26*c* (see FIG. 3). Signal lines 28*a* (see FIG. 3) of the signal cable 28 are electrically connected to the connection terminals.

The circuit board 26 is formed of, for example, a flexible substrate, and is formed of, for example, a flexible print substrate.

The imaging element 25 is mounted on the front surface 26*f* of the first plane portion 26*a*, as shown in FIG. 3. In addition, the electronic component 30 may be mounted on the front surface 26*f* of the first plane portion 26*a*.

The electronic component 30 is mounted on a back surface 26*g* of the second plane portion 26*c* facing the front surface 26*f* of the first plane portion 26*a*. Since the second plane portion 26*c* is inclined with respect to the first plane portion 26*a*, a region having a wide space is formed between the first plane portion 26*a* and the second plane portion 26*c*. Therefore, the electronic component 30 having a large size can be mounted. For example, in the back surface 26*g* of the second plane portion 26*c*, the electronic component 30 whose height is higher than a height of the electronic component 30 mounted on the first bent portion 26*b* side can be mounted on the second bent portion 26*d* side. In this way, electronic components having various sizes can be mounted, and the space of the endoscope imaging apparatus 20 can be effectively utilized.

As described above, the connection terminals (not shown) are provided on the back surface 26*h* of the third plane portion 26*e* facing the second plane portion 26*c*. The electronic component 30 is mounted on a front surface 26*i* of the third plane portion 26*e*. The disposition of the imaging element 25, the electronic component 30, the connection terminals, and the like on the circuit board 26 is not particularly limited.

The signal lines 28*a* (see FIG. 3) of the signal cable 28 are electrically connected to the connection terminals provided in the back surface 26*h* (see FIG. 3) of the third plane portion 26*e* of the circuit board 26, and the imaging element 25 and the signal cable 28 are electrically connected to each other. Light is converted into an electrical signal by the imaging element 25, and this electrical signal is transmitted via the signal cable 28. The signal cable 28 is inserted into the insertion part, the operating part, the universal cord, or the like of the endoscope, and is electrically connected to the processor device 16 (see FIG. 1).

The signal cable 28 is not particularly limited as long as the signal cable 28 has the signal lines 28*a* and an outer covering 28*d* constituting an outer periphery thereof. For example, as shown in FIG. 3, the signal cable 28 has a plurality of the signal lines 28*a*, a coating layer 28*b* that covers each signal line 28*a*, a shielded conductor 28*c* provided around all of the plurality of signal lines 28*a* covered with the coating layers 28*b*, and the outer covering 28*d* that covers the shielded conductor 28*c*. The signal cable 28 is a multi-core cable into which the plurality of signal lines 28*a* are bundled, around which the shielded conductor 28*c* is provided, and which is accommodated inside the cylindrical outer covering 28*d*.

As described above, the outer covering 28*d* constitutes the outer periphery of the signal cable 28. The coating layer 28*b*, the shielded conductor 28*c*, and the outer covering 28*d* each have, for example, a cylindrical shape. In addition, the shielded conductor 28*c* of the signal cable 28 is referred to as a shield. The signal cable 28 has, for example, five signal lines 28*a*. The number of the signal lines 28*a* depends on the configuration of the endoscope imaging apparatus 20, is not particularly limited, and may be two, three, four, or six or more.

In addition, for example, the outer covering 28*d* (see FIG. 3) of the signal cable 28 may be covered with, for example, a protective tube (not shown). The protective tube protects the signal cable 28, prevents the signal cable 28 from breaking, and prevents the signal lines 28*a* from being disconnected.

The prism 27 is disposed between the lens barrel 22 and the imaging element 25 via a cover glass 31. The prism 27 guides light that has passed through the imaging lens 23 to the light-receiving surface 25*a* of the imaging element 25. The prism 27 is, for example, a right-angle prism in which the incident surface 27*a* and an emission surface 27*b* are orthogonal to each other. In addition, the prism 27 has an inclined surface 27*c* that connects the incident surface 27*a* and the emission surface 27*b*. The inclined surface 27*c* is a reflecting surface 27*e* of the prism 27.

The prism 27 is an optical element that bends the optical axis C of the imaging lens 23 by 90° to make light that has transmitted through the imaging lens 23 incident on the imaging element 25. The prism 27 bends light that has passed through the imaging lens 23 held by the lens barrel 22 on the inclined surface 27*c*, that is, on the reflecting surface 27*e* by 90° to change an optical path, and guides the light to the light-receiving surface 25*a* of the imaging element 25. The light that has transmitted through the imaging lens 23 is incident into the prism 27, is reflected by the inclined surface 27*c* of the prism 27, that is, by the reflecting surface 27*e*, and is incident on the light-receiving surface 25*a* of the imaging element 25 after the optical path is bent by 90°. The light that has transmitted through the imaging lens 23 is light including information on the observation target.

For example, the prism 27 is disposed such that the incident surface 27*a* faces a surface on a base end side of the lens barrel 22. In addition, the prism 27 is disposed such that the emission surface 27*b* faces the light-receiving surface 25*a* of the imaging element 25. In this case, the prism 27 is disposed on the cover glass 31 such that the emission surface 27*b* faces the cover glass 31.

The cover glass 31 is disposed on the light-receiving surface 25*a* of the imaging element 25, and protects the light-receiving surface 25*a*. The prism 27 and the cover glass 31 are bonded to each other with, for example, a photocurable adhesive. A configuration may be adopted in which no cover glass 31 is provided.

The holder 24 is a member that holds the lens barrel 22 and the prism 27, and the holder 24 is a substantially tubular member. The holder 24 has, for example, a polygonal flange portion 24*b* provided on an edge surface on the base end side of a mounting tube portion 24*a*.

The lens barrel 22 is fitted inside the mounting tube portion 24*a* to hold the lens barrel 22. An inner surface of the mounting tube portion 24*a* of the holder 24 and an outer peripheral surface of the lens barrel 22 are bonded and fixed.

As an adhesive for bonding the holder 24 and the lens barrel 22 to each other, various known adhesives used in an endoscope in the related art can be used. This point is also the same for the adhesive for bonding other members to each other.

A holding part 24*c* that holds the prism 27 is provided on the flange portion 24*b*. The holding part 24*c* has a pair of holding members 24*d* that holds the prism 27 (optical element). The holding members 24*d* are respectively provided at both ends of the flange portion 24*b* in the Y direction, and the holding members 24*d* are disposed to face each other in the Y direction.

The prism 27 is disposed between the holding members 24*d*, and the incident surface 27*a* is in contact with the flange portion 24*b* in a state of being interposed between the holding members 24*d*. With this, the prism 27 is positioned in the X direction. The pair of holding members 24*d* also functions as a restricting member that regulates a position of the prism 27.

The holder 24 holds the lens barrel 22 and the prism 27 at predetermined positions, so that relative positions of the lens barrel 22 and of the prism 27, that is, the relative positions of the lens barrel 22 and the light-receiving surface 25*a* of the imaging element 25 are fixed. The emission surface 27*b* of the prism 27 and the imaging element 25 face each other. Although the two holding members 24*d* have different thicknesses, the holding member 24*d* of the holder 24 will be described in detail below.

Here, the relative position of the lens barrel 22 with respect to the holder 24 in an optical axis direction of the imaging lens 23 is adjusted so as to be in focus on the light-receiving surface 25*a* of the imaging element 25, so that the lens barrel 22 is bonded and fixed to the holder 24. The optical axis direction is an extending direction of the optical axis C of the imaging lens 23. The optical axis direction of the imaging lens 23 is a direction parallel to the X direction.

As described above, the forceps pipe 17 is connected to the forceps port 13*a* (see FIG. 2), and the forceps pipe 17 is disposed on the light-receiving surface 25*a* side of the imaging element 25.

As shown in FIG. 4, in the endoscope imaging apparatus 20, in a case in which the endoscope imaging apparatus 20 is viewed in the first direction perpendicular to the light-receiving surface 25*a* of the imaging element 25, a central axis CL of the imaging element that passes through a center Cs (see FIG. 7) of an outer shape of the imaging element 25 and is parallel to the optical axis C of the imaging lens 23 is located closer to the forceps port 13*a* side (see FIG. 2) than the optical axis C of the imaging lens 23 is. A part of the forceps pipe 17 connected to the forceps port 13*a* overlaps the light-receiving surface 25*a* of the imaging element 25, and a central axis Cc of the forceps pipe 17 is located outside the imaging element 25. For example, the forceps pipe 17 connected to the forceps port 13*a*, the central axis Cc is disposed such that the central axis Cc is parallel to the optical axis C of the imaging lens 23.

Further, on a plane PA (see FIGS. 5 and 6) that passes through the optical axis C of the imaging lens 23 and is parallel to the light-receiving surface 25*a* of the imaging element 25, a part farthest from the optical axis C of the imaging lens 23 is opposite to the central axis CL of the imaging element 25 with respect to the optical axis C of the imaging lens 23 in a case in which the endoscope imaging apparatus 20 is viewed in the first direction.

In this case, for example, in the holder 24, the flange portion 24*b* and the mounting tube portion 24*a* are disposed such that a center of the mounting tube portion 24*a*, that is, the optical axis C of the imaging lens 23 and a center of the flange portion 24*b* are offset in the Y direction. Therefore, the inside of the distal end portion 12*a* (see FIG. 1) of the endoscope 12 (see FIG. 1) can be effectively used. Accordingly, it is possible to realize the endoscope 12 (see FIG. 1) with a narrower diameter of the distal end portion 12*a* (see FIG. 1) of the insertion part to be inserted into the body of the subject.

The forceps tube is connected to the forceps pipe 17, and the forceps pipe 17 and the forceps tube are disposed on the light-receiving surface 25*a* side of the imaging element 25. In this case, as with the forceps pipe 17 described above, a configuration may be adopted in which a part of the forceps tube overlaps the light-receiving surface 25*a* of the imaging element 25 and a central axis of the forceps tube is located outside the imaging element 25.

The above-described part farthest from the optical axis C of the imaging lens 23 is a part farthest from the optical axis C in a direction orthogonal to the optical axis C in the plane PA. For example, in FIGS. 5 and 6, an end 24*f* of the holding member 24*d* at a distance D1, which will be described below, is located at a position farther from the optical axis C than an end 24*e* of the holding member 24*d* at a distance $D_A$. The above-described part corresponds to, for example, the end 24*f* of the holding member 24*d*. The above-described part is not limited to the end 24*f* of the holding member 24*d* as long as it is a constituent member of the endoscope imaging apparatus on the plane PA, and may be one point of the member, a line such as an outline of the member, and a surface of the member.

In addition, the distance from the optical axis C is a length in a direction orthogonal to the optical axis C in the plane PA. The direction orthogonal to the optical axis C in the plane PA is the Y direction in FIGS. 5 and 6.

In addition, in a case in which the endoscope imaging apparatus 20 is viewed in the first direction as shown in FIG. 6, on the plane PA that passes through the optical axis C of the imaging lens 23 and is parallel to the light-receiving surface 25*a* of the imaging element 25, a distance between the optical axis C of the imaging lens 23 and the part farthest from the optical axis C of the imaging lens 23 is denoted by D1. In a case in which the endoscope imaging apparatus 20 is viewed in the first direction, a distance between the optical axis C of the imaging lens 23 and a first end portion 25*b* of the imaging element 25, which is located on the same side as the central axis CL of the imaging element 25, with respect to the optical axis C of the imaging lens 23 is denoted by D2. In this case, it is preferable that D1<D2.

By setting D1<D2, a space on an inner surface side of the distal end portion 12*a* (see FIG. 2) of the endoscope 12 (see FIG. 1) can be effectively used.

The distances D1 and D2 described above are shown in FIG. 5 as well as in FIG. 6. The above-described distance D1 is, for example, a distance between the optical axis C of the imaging lens 23 and the end 24*f* of the holding member 24*d* in FIGS. 5 and 6.

In the above-described case, the distance D1, the distance D2, and the distance D A can be specified by specifying the optical axis C of the imaging lens 23, the ends 24*e* and 24*f* of the holding member 24*d*, and the first end portion 25*b* of the imaging element 25.

In addition, in a case in which the endoscope imaging apparatus 20 is viewed in the first direction as shown in FIG. 6, on the plane PA (see FIGS. 5 and 6) that passes through the optical axis C of the imaging lens 23 and is parallel to the light-receiving surface 25*a* of the imaging element 25, a distance between the optical axis C of the imaging lens 23 and the part farthest from the optical axis C of the imaging lens 23 is denoted by D1 as described above. A distance between the optical axis C of the imaging lens 23 and a second end portion 25*c* (see FIG. 5) of the imaging element 25, which is located on an opposite side to the central axis CL of the imaging element 25, with respect to the optical axis C of the imaging lens 23 is denoted by D3 (see FIG. 5). In this case, it is preferable that D1-D3>0. That is, it is preferable that the distance D1 is longer than the distance D3.

By setting D1-D3>0, for example, as shown in FIG. 5, the space on the inner surface side of the distal end portion 12*a* (see FIG. 2) of the endoscope 12 (see FIG. 1) can be effectively used by offsetting the holding part 24*c* to the second end portion 25*c* side of the imaging element 25.

The distance D1 and the distance D3 are limited by an inner diameter of the distal end portion 12*a* of the endoscope 12. Therefore, an upper limit of the distances D1-D3 is appropriately determined according to the inner diameter of the distal end portion 12*a*.

In the above-described case, the distance D3 can be specified by specifying the optical axis C of the imaging lens 23 and the second end portion 25*c* of the imaging element 25.

In addition, it is preferable that, in a case in which the endoscope imaging apparatus 20 is viewed in the first direction, a central axis Cf of a maximum outer shape W (see FIG. 5) in the holding part 24*c* of the holder 24 that holds the prism 27 is parallel to the optical axis C of the imaging lens 23, and is opposite to the central axis CL of the imaging element 25 with respect to the optical axis C of the imaging lens 23. Even in this case, for example, the space on the inner surface side of the distal end portion 12*a* (see FIG. 2) of the endoscope 12 (see FIG. 1) can be effectively used by offsetting the holding part 24*c* to the second end portion 25*c* side of the imaging element 25.

The center Cs of the outer shape of the imaging element 25 is a center of an outer shape of the light-receiving surface 25*a* of the imaging element 25. In a case in which the light-receiving surface 25*a* is quadrangular, the center Cs of the outer shape of the imaging element 25 is an intersection of diagonal lines (not shown) of the light-receiving surface 25*a*.

The central axis CL of the imaging element 25 is specified by specifying the center Cs of the outer shape of the imaging element 25.

In addition, the central axis Cf of the maximum outer shape W is an axis that passes through an intermediate point in a length direction of the maximum outer shape W and is parallel to the optical axis C of the imaging lens 23. The length direction of the maximum outer shape W is the Y direction in FIG. 5.

The maximum outer shape W is obtained by measuring a corresponding portion in the maximum outer shape W in the holding part 24*c* of the holder 24 using a caliper or a micrometer.

In addition, in a case in which the endoscope imaging apparatus 20 is viewed in the first direction, as shown in FIG. 4, the optical axis C of the imaging lens 23, the central axis CL passing through the center Cs of the outer shape of the imaging element 25, and the central axis Cf of the holder 24 are parallel to each other.

In a direction orthogonal to the optical axis C of the imaging lens 23, that is, in the Y direction in FIG. 4, a distance between the central axis CL of the imaging element 25 and the optical axis C of the imaging lens 23 is defined as a first distance $\alpha_1$, and a distance between the optical axis C of the imaging lens 23 and the central axis Cf of the maximum outer shape W in the holding part 24*c* of the holder 24 is defined as a second distance $\alpha_2$. In this case, it is preferable that the first distance α1 is longer than the second distance $\alpha_2$.

In a case in which the first distance α1 is longer than the second distance $\alpha_2$, the imaging element 25 is disposed offset to the forceps pipe 17 side. Therefore, the imaging element 25 with a larger size can be disposed. For this reason, it is preferable that the first distance α1 is longer than the second distance $\alpha_2$.

The first distance α1 and the second distance $\alpha_2$ can be specified by specifying the central axis CL of the imaging element 25, the central axis Cf of the holder 24, and the optical axis C of the imaging lens 23.

As described above, the endoscope imaging apparatus 20 has the circuit board 26 to which the imaging element 25 is electrically connected. The circuit board 26 at least has the first plane portion 26*a* on which the imaging element 25 is mounted, and the second plane portion 26*c* connected by the first plane portion 26*a* and the first bent portion 26*b*.

Figure 7:
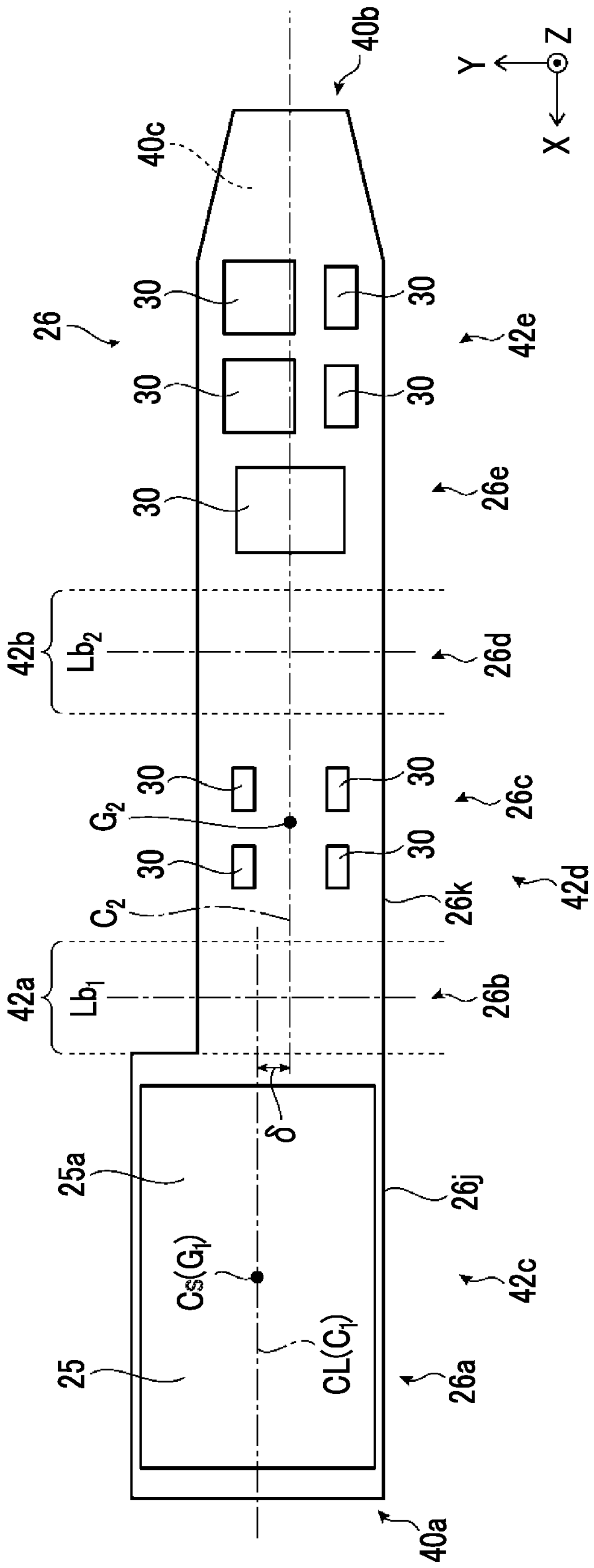
FIG. 7 is a schematic plan view showing an example of a circuit board of an example of the endoscope imaging apparatus according to the embodiment of the present invention.

An axis that passes through a center $G_1$ (see FIG. 7) of an outer shape of the first plane portion 26*a* and is parallel to the optical axis C of the imaging lens 23 is defined as a first axis $C_1$ (see FIG. 7). An axis that passes through a center $G_2$ (see FIG. 7) of an outer shape of the first bent portion 26*b* and the second plane portion 26*c* and is parallel to the optical axis C of the imaging lens 23 is defined as a second axis $C_2$ (see FIG. 7). The first axis $C_1$ and the second axis $C_2$ are parallel to each other, and the second axis $C_2$ is opposite to the first axis $C_1$ with the optical axis C of the imaging lens 23 interposed therebetween. A difference in the Y direction between the first axis $C_1$ and the second axis $C_2$ is δ. That is, the first axis $C_1$ and the second axis $C_2$ are deviated by the difference δ.

In the circuit board 26, the first axis $C_1$ and the second axis $C_2$ are configured as described above, so that the circuit board 26 is disposed offset to the opposite side of the forceps pipe 17, and the electronic component 30 can be disposed in a region Ds shown in FIG. 5. For this reason, many electronic components 30 can be disposed within a range of the maximum outer shape W of the flange portion 24*b*.

As described above, in a case in which the second axis $C_2$ (see FIG. 7) is opposite to the first axis $C_1$ with the optical axis C of the imaging lens 23 interposed therebetween, for example, one side surface 26*j* of the first plane portion 26*a* and one side surface 26*k* of the first bent portion 26*b* and the second plane portion 26*c* are disposed in the same plane.

The center G 1 (see FIG. 7) of the outer shape of the first plane portion 26*a* is an intersection of diagonal lines (not shown) of the first plane portion 26*a* in a case in which the first plane portion 26*a* is quadrangular.

In a case in which the first bent portion 26*b* and the second plane portion 26*c* are quadrangular in an expanded state, the center $G_2$ (see FIG. 7) of the outer shape of the first bent portion 26*b* and the second plane portion 26*c* is an intersection of diagonal lines (not shown) of a quadrangle configured of the expanded first bent portion 26*b* and second plane portion 26*c*.

The first axis $C_1$ can be specified by specifying the center $G_1$ of the outer shape of the first plane portion 26*a* described above. The second axis $C_2$ can be specified by specifying the center $G_2$ of the outer shape of the first bent portion 26*b* and the second plane portion 26*c* described above.

In addition, it is preferable that, in a case in which the endoscope imaging apparatus 20 is viewed in the first direction, the central axis Cf of the maximum outer shape W (see FIG. 5) in the holding part 24*c* of the holder 24 coincides with the second axis $C_2$ of the circuit board 26. Accordingly, as shown in FIG. 4, the circuit board 26 is accommodated in the width of the holding part 24*c* of the holder 24. Thereby, the width of the endoscope imaging apparatus 20 can be minimized, that is, the length of the endoscope imaging apparatus 20 in the Y direction can be minimized.

The coincidence between the central axis Cf of the holder 24 and the second axis $C_2$ of the circuit board 26 means that a distance between the central axis Cf of the holder 24 and the second axis $C_2$ of the circuit board 26 in the Y direction is 0.2 mm or less.

The coincidence between the central axis Cf of the holder 24 and the second axis $C_2$ of the circuit board 26 means that the axes are not deviated ideally, that is, the distance between the central axis Cf of the holder 24 and the second axis $C_2$ of the circuit board 26 in the Y direction is 0 mm.

In a case in which the center Cs of the outer shape of the imaging element 25 coincides with the center $G_1$ of the outer shape of the first plane portion 26*a* of the circuit board 26, and the imaging element 25 is mounted on the first plane portion 26*a* of the circuit board 26, the first axis $C_1$ coincides with the center axis CL passing through the center Cs of the outer shape of the imaging element 25. In this case, the difference δ in FIG. 7 is the total length of the first distance $\alpha_1$ and the second distance $\alpha_2$ shown in FIG. 4.

As described above, the holding part 24*c* of the holder 24 has the pair of holding members 24*d* that holds the prism 27. It is preferable that each of the pair of holding members 24*d* is different in thickness, for example, out of the pair of holding members 24*d*, a thickness $d_1$ of a holding member 24*d* on the second axis $C_2$ side of the circuit board 26 with respect to the central axis Cf of the maximum outer shape W in the holding part 24*c* of the holder 24 is thicker. That is, it is preferable that, between a thickness $d_2$ of the holding member 24*d* on the central axis CL side of the imaging element 25 in the holding part 24*c* of the holder 24 and the thickness d1 of the holding member 24*d* on the second axis $C_2$ side, the thickness d1 of the holding member 24*d* is thicker. Accordingly, the strength of the holder 24 is increased, and the prism 27 can be held more reliably.

The thickness d1 of the holding member 24*d* and the thickness $d_2$ of the holding member 24*d* described above are obtained by measuring a corresponding portion in the holding part 24*c* of the holder 24 using a caliper or a micrometer.

As described above, in the holder 24, the center of the mounting tube portion 24*a* and the center of the flange portion 24*b* are offset in the Y direction. Therefore, in order to dispose the prism 27 in alignment with the optical axis C of the imaging lens 23, the prism 27 also needs to be disposed by being offset in the Y direction with respect to the flange portion 24*b*. In this case, the prism 27 can be disposed in alignment with the optical axis C of the imaging lens 23 by making the thickness $d_1$ of the holding member 24*d* on the second axis $C_2$ side of the circuit board 26 thicker as described above.

The thickness of the holding member 24*d* is a length in the Y direction. The thickness of the holding member 24*d* can be specified by measuring the length of the holding member 24*d* in the Y direction using a caliper or a micrometer.

In the holder 24, the two holding members 24*d* have different thicknesses but the same size and shape, that is, the two holding members 24*d* are congruent, but not limited to this, and the two holding members 24*d* may have different sizes and shapes.

In addition, in the holder 24, the shape of the outer shape of the holding member 24*d* is a pentagon in FIG. 3, but is not particularly limited, and may be a circle, an ellipse, or a polygon, such as a triangle, a quadrangle, or a hexagon, or may be a shape formed by combining these shapes. Furthermore, not only one shape but also a plurality of shapes having the same shape may be disposed or a specific pattern may be used, but it is preferable to have at least three side surfaces.

The size of the holding member 24*d* of the holder 24 is preferably, for example, a size for covering at least a part of a side surface 27*d* of the prism 27. The size of the holding member 24*d* is set to the size for covering at least a part of the side surface 27*d* of the prism 27, so that the prism 27 can be more stably interposed and fixed, and stable position restriction can be performed. In addition, this can be used for positioning the prism in the Y direction with respect to the holder during assembly.

An upper limit of the size of the holding member 24*d* of the holder 24 can be a size for covering the entire side surface 27*d* of the prism 27.

In the holder 24, although a configuration is adopted in which the pair of holding members 24*d* is provided, the present invention is not limited to this as long as the size is not increased, and the number of the holding members can be three or more.

Here, FIG. 7 is a schematic plan view showing an example of a circuit board of an example of the endoscope imaging apparatus according to the embodiment of the present invention. In FIG. 7, the same constituents as those of the endoscope imaging apparatus 20 shown in FIGS. 3 to 6 are denoted by the same reference numerals, and detailed descriptions thereof will be omitted.

FIG. 7 shows the circuit board 26 in a state before being folded, and shows a state in which the circuit board 26 is expanded. The circuit board 26 in a state before being folded has a first bending region 42*a* and a second bending region 42*b*. The first bending region 42*a* is a region where the first bent portion 26*b* is formed, and the second bending region 42*b* is a region where the second bent portion 26*d* is formed.

In the circuit board 26 in a state before being folded, a region between a distal end 40*a* of the circuit board 26 and the first bending region 42*a* is a region 42*c* where the first plane portion 26*a* is formed. The imaging element 25 is mounted in the region 42*c*.

A region between the first bending region 42*a* and the second bending region 42*b* is a region 42*d* where the second plane portion 26*c* is formed. A plurality of the electronic components 30 are mounted in the region 42*d*.

A region on a rear end 40*b* side with respect to the second bending region 42*b* is a region 42*e* where the third plane portion 26*e* is formed. A plurality of the electronic components 30 are mounted in the region 42*e*.

In the circuit board 26 shown in FIG. 7, the first bending region 42*a* is bent such that the imaging element 25 and the electronic components 30 and 30 face each other, and the second bending region 42*b* is bent such that back surfaces 40*c* of the circuit board 26 face each other. Accordingly, as shown in FIG. 3, the circuit board 26 has a configuration in which the first bent portion 26*b* and the second bent portion 26*d* are provided. For example, in a case of bending the first bending region 42*a*, the first bending region 42*a* is bent based on a first folding surface $Lb_1$. In addition, for example, in a case of bending the second bending region 42*b*, the second bending region 42*b* is bent based on a second folding surface $Lb_2$. In this way, the circuit board 26 is bent at the plurality of bending regions. In FIG. 7, the first folding surface $Lb_1$ and the second folding surface $Lb_2$ are parallel to each other, but the present invention is not limited to this, and may not be parallel to each other. Since the first folding surface $Lb_1$ is provided in the first bending region 42*a* and the second folding surface $Lb_2$ is provided in the second bending region 42*b*, the first folding surface $Lb_1$ and the second folding surface $Lb_2$ are not orthogonal to each other.

It is preferable that folding directions of the circuit board 26 are all the same direction. Accordingly, there is no bending region in the Y direction of the endoscope imaging apparatus 20 like the first bent portion 26*b* and the second bent portion 26*d*, and the proportion occupied by the bending region in the space inside the endoscope imaging apparatus 20 can be reduced.

In addition, in the circuit board 26, it is preferable that a maximum width $W_2$ of the second plane portion 26*c* is narrower than a maximum width $W_1$ of the first plane portion 26*a* because the first bending region 42*a* is easily bent and the first bent portion 26*b* is easily formed. Furthermore, the closer to the imaging element 25, the more complicated the circuit is, and thus a large mounting area is required, so that it is preferable that the maximum width $W_2$ of the second plane portion 26*c* is narrower than the maximum width $W_1$ of the first plane portion 26*a*. That is, it is preferable that the maximum width $W_1$ of the first plane portion 26*a* is wider than the maximum width $W_2$ of the second plane portion 26*c*.

The maximum width $W_1$ of the first plane portion 26*a* and the maximum width $W_2$ of the second plane portion 26*c* described above are both obtained by measuring a corresponding portion in the circuit board 26 using a caliper or a micrometer.

In the endoscope imaging apparatus 20, an observational image captured by the imaging element 25 from the imaging lens 23 is formed on the light-receiving surface 25*a* of the imaging element 25 and converted into an electrical signal, and this electrical signal is output to the processor device 16 (see FIG. 1) via the signal cable 28 and is converted into a video signal, and an observation image is displayed on the monitor connected to the processor device 16.

In the endoscope imaging apparatus 20, as shown in FIG. 3, the inclined surface 27*c* of the prism 27 faces the second bent portion 26*d*. It is preferable that at least a part of the second bent portion 26*d* of the circuit board 26 overlaps the inclined surface 27*c* of the prism 27 when viewed from a direction perpendicular to the light-receiving surface 25*a* of the imaging element 25, that is, from the Z direction in FIG. 3. With this, the second bent portion 26*d* enters a space on an inclined surface 27*c* side of the prism 27, and the space on the inclined surface 27*c* side of the prism 27 is effectively used so that a length of the endoscope imaging apparatus 20 in the direction of the optical axis can be shortened and the endoscope imaging apparatus 20 can be miniaturized in the direction of the optical axis.

In the endoscope imaging apparatus 20, it is preferable that a part of the inclined surface 27*c* of the prism 27 and a part of the second bent portion 26*d* of the circuit board 26 are connected to each other by a photocurable adhesive (not shown), and that a part of the first bent portion 26*b* and/or a part of the second plane portion 26*c*, and a part of the signal cable 28 and/or the third plane portion 26*e* are connected to each other by a photocurable adhesive (not shown). With this, the shape of the circuit board 26 can be maintained, and the manufacturing time of the endoscope imaging apparatus 20 can be shortened.

The photocurable adhesive is, for example, an adhesive that is cured by ultraviolet light having a wavelength of about 100 to 400 nm, visible light having a wavelength of about more than 400 and less than 780 nm, infrared light having a wavelength of about 780 nm to 1 mm, or the like. The photocurable adhesive is, for example, an epoxy resin-based photocurable adhesive, an acrylic resin-based photocurable adhesive, or a silicone-based photocurable adhesive. In addition, an adhesive in which photo-curing and heat-curing are used in combination may be used. This photocurable adhesive can also be used for the above-described bonding between the prism 27 and the cover glass 31.

Further, the prism 27 (optical element), the circuit board 26, or the electronic component 30 may be covered with a resin so as not to be exposed. As the resin, the above-described photocurable adhesive may be used as it is. In addition to the photocurable adhesive, a thermosetting adhesive or an adhesive in which photo-curing and heat-curing are used in combination may be used as the resin. In addition, it is preferable that the exposed portions of the prism 27 and the cover glass 31 are covered with a resin having a low light transmittance.

Both the first bent portion 26*b* and the second bent portion 26*d* are formed of a curved surface. Curvature radii of the first bent portion 26*b* and the second bent portion 26*d* may be the same as or different from each other. In FIG. 3, the first bent portion 26*b* and the second bent portion 26*d* have the same curvature radius. The curvature radii of the first bent portion 26*b* and of the second bent portion 26*d* are adjusted, so that a space between the first plane portion 26*a* and the second plane portion 26*c*, and a space between the second plane portion 26*c* and the third plane portion 26*e* can be adjusted.

The first bent portion 26*b* and the second bent portion 26*d* are not limited to being configured only by a curved surface as long as a curved surface is provided, and for example, a configuration may be adopted in which the first bent portion 26*b* and the second bent portion 26*d* each have a plane and a curved surface.

The curvature radius is obtained as follows. First, an image of the circuit board 26 from a side surface direction is acquired. The acquired image is used to specify a corresponding portion corresponding to each of the curvature radii of the first bent portion 26*b* and of the second bent portion 26*d*. A curve is fitted to the corresponding portion, and the curvature radius of the curve is measured by using a ruler. The measured value is the curvature radius.

The above-described measurement of the curvature radius also includes taking the acquired image of the circuit board 26 into the computer and using software to measure the curvature radii of the first bent portion 26*b* and the second bent portion 26*d*. Fitting the curve to the corresponding portion corresponding to the curvature radius and measuring the curvature radius of the curve by using a ruler also includes performing the measurement by using software on the computer.

The present invention is basically configured as described above. Hereinabove, the endoscope according to the embodiment of the present invention has been described in detail. However, the present invention is not limited to the above-described examples, and various improvements or modifications may be made within a range not departing from the scope of the present invention.

EXPLANATION OF REFERENCES

10: endoscope system
12: endoscope
12*a*: distal end portion
12*b*: distal end surface
13*a*: forceps port
13*b*: imaging unit
13*c*: light guide
14: light source device
16: processor device
17: forceps pipe
20: endoscope imaging apparatus
22: lens barrel
23: imaging lens
24: holder
24*a*: mounting tube portion
24*b*: flange portion
24*c*: holding part
24*d*: holding member
24*e*, 24*f*: end
25: imaging element
25*a*: light-receiving surface
25*b*: first end portion
25*c*: second end portion
26: circuit board
26*a*: first plane portion
26*b*: first bent portion
26*c*: second plane portion
26*d*: second bent portion
26*e*: third plane portion
26*f*: front surface
26*g*, 26*h*: back surface
26*j*, 26*k*: side surface
27: prism
27*a*: incident surface
27*b*: emission surface
27*c*: inclined surface
27*e*: reflecting surface
28: signal cable
28*a*: signal line
28*b*: coating layer
28*c*: shielded conductor
28*d*: outer covering
30: electronic component
31: cover glass
32: bump
40*a*: distal end
40*b*: rear end
40*c*: back surface
42*a*: first bending region
42*b*: second bending region
42*c*, 42*d*, 42*e*: region
C: optical axis
$C_1$: first axis
$C_2$: second axis
CL, Cc, Cf: central axis
Cs, $G_1$, $G_2$: center
$D_A$, D1, D2, D3: distance
Ds: region
$Lb_1$: first folding surface
$Lb_2$ second folding surface
W: maximum outer shape
$W_1$: maximum width
$W_2$: maximum width
$\alpha_1$: first distance
$\alpha_2$: second distance

What is claimed is:

1. An endoscope comprising:
a forceps port; and
an imaging unit, wherein at least the forceps port and the imaging unit are disposed side by side at a distal end of the endoscope, the imaging unit includes an imaging lens, an imaging element having a light-receiving surface disposed parallel to an optical axis of the imaging lens, an optical element that bends the optical axis of the imaging lens by 90° to make light that has transmitted through the imaging lens incident on the imaging element, and a holder that holds the imaging lens and the optical element, a forceps pipe is connected to the forceps port, a forceps tube is connected to the forceps pipe, and the forceps pipe and the forceps tube are disposed on a light-receiving surface side, in a case in which the imaging unit is viewed in a first direction perpendicular to the light-receiving surface of the imaging element, a central axis of the imaging element that passes through a center of an outer shape of the imaging element and is parallel to the optical axis of the imaging lens is located closer to a forceps port side of the imaging unit than the optical axis of the imaging lens is, a part of the forceps pipe connected to the forceps port or the forceps tube overlaps the light-receiving surface of the imaging element, and a central axis of each of the forceps pipe and the forceps tube is located outside the imaging element, and on a plane that passes through the optical axis of the imaging lens and is parallel to the light-receiving surface of the imaging element, a part of the holder farthest from the optical axis of the imaging lens is opposite to the central axis of the imaging element with respect to the optical axis of the imaging lens in a case in which the imaging unit is viewed in the first direction.

2. The endoscope according to claim 1, wherein D1<D2 is satisfied in a case in which D1 is a distance between the optical axis of the imaging lens and the part farthest from the optical axis of the imaging lens on the plane that passes through the optical axis of the imaging lens and is parallel to the light-receiving surface of the imaging element in a case in which the imaging unit is viewed in the first direction, and D2 is a distance between the optical axis of the imaging lens and a first end portion of the imaging element, which is located on a same side as the central axis of the imaging element, with respect to the optical axis of the imaging lens in a case in which the imaging unit is viewed in the first direction.

3. The endoscope according to claim 1, wherein D1−D3>0 is satisfied in a case in which D1 is a distance between the optical axis of the imaging lens and the part farthest from the optical axis of the imaging lens on the plane that passes through the optical axis of the imaging lens and is parallel to the light-receiving surface of the imaging element in a case in which the imaging unit is viewed in the first direction, and D3 is a distance between the optical axis of the imaging lens and a second end portion of the imaging element, which is located on an opposite side to the central axis of the imaging element, with respect to the optical axis of the imaging lens.

4. The endoscope according to claim 2, wherein D1−D3>0 is satisfied in a case in which D3 is a distance between the optical axis of the imaging lens and a second end portion of the imaging element, which is located on an opposite side to the central axis of the imaging element, with respect to the optical axis of the imaging lens.

5. The endoscope according to claim 1, wherein, in a case in which the imaging unit is viewed in the first direction, a central axis of a maximum outer shape in a holding part of the holder that holds the optical element is parallel to the optical axis of the imaging lens, and is opposite to the central axis of the imaging element with respect to the optical axis of the imaging lens.

6. The endoscope according to claim 2, wherein, in a case in which the imaging unit is viewed in the first direction, a central axis of a maximum outer shape in a holding part of the holder that holds the optical element is parallel to the optical axis of the imaging lens, and is opposite to the central axis of the imaging element with respect to the optical axis of the imaging lens.

7. The endoscope according to claim 3, wherein, in a case in which the imaging unit is viewed in the first direction, a central axis of a maximum outer shape in a holding part of the holder that holds the optical element is parallel to the optical axis of the imaging lens, and is opposite to the central axis of the imaging element with respect to the optical axis of the imaging lens.

8. The endoscope according to claim 5, wherein, in a case in which the imaging unit is viewed in the first direction, the optical axis of the imaging lens, the central axis of the imaging element, and the central axis of a maximum outer shape in a holding part of the holder are parallel to each other, and in a case in which a distance between the central axis of the imaging element and the optical axis of the imaging lens is a first distance, and a distance between the optical axis of the imaging lens and the central axis of the maximum outer shape in the holding part of the holder is a second distance in a direction orthogonal to the optical axis of the imaging lens, the first distance is longer than the second distance.

9. The endoscope according to claim 1, wherein a circuit board to which the imaging element is electrically connected is provided, the circuit board includes at least a first plane portion on which the imaging element is mounted and a second plane portion connected to the first plane portion by a first bent portion, and a first axis that passes through a center of an outer shape of the first plane portion and is parallel to the optical axis of the imaging lens and a second axis that passes through a center of an outer shape of the first bent portion and the second plane portion and is parallel to the optical axis of the imaging lens are parallel to each other, and the second axis is opposite to the first axis with the optical axis of the imaging lens interposed therebetween.

10. The endoscope according to claim 2, wherein a circuit board to which the imaging element is electrically connected is provided, the circuit board includes at least a first plane portion on which the imaging element is mounted and a second plane portion connected to the first plane portion by a first bent portion, and a first axis that passes through a center of an outer shape of the first plane portion and is parallel to the optical axis of the imaging lens and a second axis that passes through a center of an outer shape of the first bent portion and the second plane portion and is parallel to the optical axis of the imaging lens are parallel to each other, and the second axis is opposite to the first axis with the optical axis of the imaging lens interposed therebetween.

11. The endoscope according to claim 3, wherein a circuit board to which the imaging element is electrically connected is provided, the circuit board includes at least a first plane portion on which the imaging element is mounted and a second plane portion connected to the first plane portion by a first bent portion, and a first axis that passes through a center of an outer shape of the first plane portion and is parallel to the optical axis of the imaging lens and a second axis that passes through a center of an outer shape of the first bent portion and the second plane portion and is parallel to the optical axis of the imaging lens are parallel to each other, and the second axis is opposite to the first axis with the optical axis of the imaging lens interposed therebetween.

12. The endoscope according to claim 5, wherein a circuit board to which the imaging element is electrically connected is provided, the circuit board includes at least a first plane portion on which the imaging element is mounted and a second plane portion connected to the first plane portion by a first bent portion, and a first axis that passes through a center of an outer shape of the first plane portion and is parallel to the optical axis of the imaging lens and a second axis that passes through a center of an outer shape of the first bent portion and the second plane portion and is parallel to the optical axis of the imaging lens are parallel to each other, and the second axis is opposite to the first axis with the optical axis of the imaging lens interposed therebetween.

13. The endoscope according to claim 8, wherein a circuit board to which the imaging element is electrically connected is provided, the circuit board includes at least a first plane portion on which the imaging element is mounted and a second plane portion connected to the first plane portion by a first bent portion, and a first axis that passes through a center of an outer shape of the first plane portion and is parallel to the optical axis of the imaging lens and a second axis that passes through a center of an outer shape of the first bent portion and the second plane portion and is parallel to the optical axis of the imaging lens are parallel to each other, and the second axis is opposite to the first axis with the optical axis of the imaging lens interposed therebetween.

14. The endoscope according to claim 9, wherein, in a case in which the imaging unit is viewed in the first direction, a central axis of a maximum outer shape in a holding part of the holder that holds the optical element coincides with the second axis of the circuit board.

15. The endoscope according to claim 5, wherein the holding part of the holder that holds the optical element includes a pair of holding members that holds the optical element, and each of the pair of holding members is different in thickness, and, out of the pair of holding members, a holding member on a second axis side of a circuit board with respect to the central axis of the maximum outer shape in the holding part of the holder is thicker.

16. The endoscope according to claim 8, wherein the holding part of the holder that holds the optical element includes a pair of holding members that holds the optical element, and each of the pair of holding members is different in thickness, and, out of the pair of holding members, a holding member on a second axis side of a circuit board with respect to the central axis of the maximum outer shape in the holding part of the holder is thicker.

17. The endoscope according to claim 9, wherein a holding part of the holder that holds the optical element includes a pair of holding members that holds the optical element, and each of the pair of holding members is different in thickness, and, out of the pair of holding members, a holding member on a second axis side of the circuit board with respect to a central axis of a maximum outer shape in the holding part of the holder is thicker.

18. The endoscope according to claim 14, wherein a holding part of the holder that holds the optical element includes a pair of holding members that holds the optical element, and each of the pair of holding members is different in thickness, and, out of the pair of holding members, a holding member on a second axis side of the circuit board with respect to a central axis of a maximum outer shape in the holding part of the holder is thicker.

* * * * *